(12) United States Patent
Asprion et al.

(10) Patent No.: US 8,766,009 B2
(45) Date of Patent: Jul. 1, 2014

(54) PROCESS FOR PREPARING ETHYLAMINES AND MONOISOPROPYLAMINE (MIPA)

(71) Applicant: BASF SE, Ludwigshafen (DE)

(72) Inventors: Norbert Asprion, Ludwigshafen (DE); Manfred Julius, Limburgerhof (DE); Oliver Bey, Niederkirchen (DE); Stefanie Werland, Mannheim (DE); Frank Stein, Bad Durkheim (DE); Matthias Kummer, Weisenheim (DE); Wolfgang Mägerlein, Mannheim (DE); Johann-Peter Melder, Böhl-Iggelheim (DE); Kevin Huyghe, Kapellen (BE); Maarten Moors, Meeuwen-Gruitrode (BE)

(73) Assignee: BASF SE (DE)

(*) Notice: Subject to any disclaimer, the term of this patent is extended or adjusted under 35 U.S.C. 154(b) by 0 days.

(21) Appl. No.: 13/682,059

(22) Filed: Nov. 20, 2012

(65) Prior Publication Data

US 2013/0131385 A1    May 23, 2013

Related U.S. Application Data

(60) Provisional application No. 61/561,953, filed on Nov. 21, 2011.

(51) Int. Cl.
*C07C 209/16* (2006.01)

(52) U.S. Cl.
USPC .......................................... 564/480; 564/479

(58) Field of Classification Search
None
See application file for complete search history.

(56) References Cited

U.S. PATENT DOCUMENTS

| | | | |
|---|---|---|---|
| 4,014,933 A | 3/1977 | Boettger et al. | |
| 4,314,084 A | 2/1982 | Martinez de Pinillos et al. | |
| 5,002,922 A | 3/1991 | Irgang et al. | |
| 5,124,295 A | 6/1992 | Nebesh et al. | |
| 5,530,127 A | 6/1996 | Reif et al. | |
| 5,536,691 A | 7/1996 | Breitscheidel et al. | |
| 7,041,857 B1 | 5/2006 | Hayes et al. | |
| 7,642,382 B2 * | 1/2010 | Gerlach et al. | 564/480 |
| 2001/0003137 A1 | 6/2001 | Nouwen et al. | |
| 2003/0013873 A1 | 1/2003 | Neumann et al. | |
| 2004/0220428 A1 | 11/2004 | Gerlach et al. | |
| 2007/0112218 A1 | 5/2007 | Meier et al. | |
| 2008/0194879 A1 | 8/2008 | Hoffer et al. | |
| 2009/0234163 A1 | 9/2009 | Gerlach et al. | |

FOREIGN PATENT DOCUMENTS

| | | |
|---|---|---|
| DE | 1953263 A1 | 2/1972 |
| EP | 0 284 398 A2 | 9/1988 |
| EP | 361755 A2 | 4/1990 |
| EP | 382049 A1 | 8/1990 |
| EP | 563327 A1 | 10/1993 |
| EP | 636409 A1 | 2/1995 |
| EP | 696572 A1 | 2/1996 |
| EP | 1106601 A1 | 6/2001 |
| EP | 1270543 A1 | 1/2003 |
| EP | 1431273 A1 | 6/2004 |
| WO | WO-92/10290 A1 | 6/1992 |
| WO | WO-2005/063681 A1 | 7/2005 |
| WO | WO-2006/097468 A1 | 9/2006 |
| WO | WO-2007/031449 A1 | 3/2007 |

OTHER PUBLICATIONS

International Search Report for PCT/EP2012/072473 dated Mar. 7, 2013.
Cho, J. H., et al., "Reductive Amination of 2-Propanol to Monoisopropylamine over Co/γ-$Al_2O_3$ Catalysts" Applied Catalysis A: General, vol. 417-418, (2012), pp. 313-319.

* cited by examiner

*Primary Examiner* — Brian J Davis
(74) *Attorney, Agent, or Firm* — Drinker Biddle & Reath LLP

(57) ABSTRACT

A process for preparing ethylamines and monoisopropylamine (MIPA), in which bioethanol is reacted with ammonia in the presence of hydrogen and of a heterogeneous catalyst to give ethylamines, said bioethanol having a content of sulfur and/or sulfur compounds of ≥0.1 ppm by weight (calculated S), and then isopropanol is reacted with ammonia in the presence of the same catalyst and in the presence of hydrogen to give MIPA.

25 Claims, No Drawings

PROCESS FOR PREPARING ETHYLAMINES AND MONOISOPROPYLAMINE (MIPA)

CROSS-REFERENCE TO RELATED APPLICATIONS

This application claims the benefit of U.S. Provisional Application No. 61/561,953, filed Nov. 21, 2011, which is incorporated herein by reference.

The invention relates to a process for preparing ethylamines and monoisopropylamine (MIPA).

Monoisopropylamine (MIPA) is, among other things, an important intermediate for production of pesticides, disinfectants, dyes, plasticizers and corrosion inhibitors, and for use in the pharmaceutical industry.

Ethylamines are suitable, inter alia, as intermediates in the production of fuel additives, surfactants, medicaments and crop protection compositions, hardeners for epoxy resins, catalysts for polyurethanes, intermediates for preparation of quaternary ammonium compounds, plasticizers, corrosion inhibitors, synthetic resins, ion exchangers, textile assistants, dyes, vulcanization accelerators and/or emulsifiers.

EP 1 106 601 A1 (BASF AG) describes a process for preparing monoisopropylamine from acetone and ammonia over a Cu/Ni/Co catalyst.

U.S. Pat. No. 7,041,857 B1 (Air Products and Chem. Inc.) teaches the hydrogenation of acetone to isopropanol in liquid phase over a sponge metal catalyst, particularly sponge nickel or sponge cobalt catalyst doped with chromium.

WO 05/063681 A (BASF AG) relates to a process for preparing an ethylamine by reacting ethanol with ammonia, a primary amine or a secondary amine in the presence of hydrogen and of a heterogeneous catalyst, using a biochemically produced ethanol (bioethanol), in which sulfur and/or sulfur compounds have been depleted beforehand by contacting with an adsorbent.

WO 06/097468 A (BASF AG) describes a process for preparing an ethylamine by reacting ethanol with ammonia, a primary amine and/or a secondary amine in the presence of hydrogen and of a heterogeneous hydrogenation/dehydrogenation catalyst, using bioethanol, and said catalyst comprising one or more metals of group VIII and/or IB of the Periodic Table and, after activation with hydrogen, having a CO absorption capacity of >100 μmol of CO/g of catalyst.

WO 07/031,449 A (BASF AG) teaches a catalytic process for preparing an ethylamine by reacting ethanol with ammonia, a primary amine or a secondary amine in the presence of hydrogen, using an ethanol which has been denatured by addition of di- and/or triethylamine.

EP 696 572 A1 (BASF AG) relates to an amination process for preparing amines from primary and secondary alcohols using a $ZrO_2$-supported Cu, Ni and Mo catalyst. Possible feedstocks are, for example, isopropanol and ammonia.

An alternative to synthetic ethanol is ethanol produced biologically or biochemically, especially by fermentation, called bioethanol. This is produced from renewable sources and is thus advantageous for ecological reasons. In addition, bioethanol is cheaper in some cases than synthetic ethanol.

In the case of use of bioethanol over many amination catalysts, much faster catalyst deactivation is observed than is the case when synthetic ethanol is used. Reasons for this include the sulfur and/or sulfur compounds present in bioethanol. This is described, for example, in "Fundamentals of Industrial Catalytic Processes", R. J. Farrauto and C. H. Bartholomew, publisher: Blackie Academic Professional, 1st edition, 1997, pages 265-337; quotation from page 267: " . . . sulfur- and arsenic-containing compounds are typical poisons for metals in hydrogenation, dehydrogenation and steam reforming reactions". In a table on page 268, particularly in the cases of Ni, Cu and Co catalysts, sulfur is specified as one of the standard catalyst poisons. The deactivation of amination catalysts with sulfur and sulfur compounds is also discussed by the abovementioned documents WO 05/063681 A and WO 06/097468 A.

Due to the faster deactivation, the synthesis has to be stopped more frequently to change the catalyst. This leads to production shutdown, increased catalyst costs and catalyst exchange, and an increased personnel requirement combined with an increased accident risk.

If bioethanol with a content of sulfur and/or sulfur compounds is used in amination processes, the catalytically active metal surface of the particular heterogeneous catalyst is covered more and more with the sulfur or sulfur compounds introduced by the bioalcohol with time. This leads to accelerated catalyst deactivation and hence to a distinct impairment of the economic viability of the particular process.

Synthetic ethanol generally has a content of sulfur and/or sulfur compounds of ≤0.1 ppm by weight (calculated S), for example determined according to Wickbold (DIN EN 41).

In a plant in which there is alternating amination of bioethanol and preparation of MIPA by alcohol/ketone amination over the same catalyst, the problem of catalyst poisoning by a content of sulfur and/or sulfur compounds in the bioethanol accordingly occurs. Thus, a catalyst exchange or catalyst activation by sulfur removal will be necessary between the two reactions.

It is an object of the present invention to overcome the disadvantages of the prior art and provide an improved, economically viable process for preparing ethylamines, i.e. mono-, di- and triethylamine, and monoisopropylamine (MIPA). The preparation process should afford both the ethylamines and the MIPA each in a high yield, space-time yield (STY) and selectivity, and additionally be particularly simple and economically viable.

(Space-time yields are reported in 'amount of product/(catalyst volume·time)' (kg/(Icat.·h)) and/or 'amount of product/(reactor volume·time)' (kg/(Ireactor·h)).

It has been recognized in accordance with the invention that, over a heterogeneous catalyst, particularly a heterogeneous copper, nickel and/or cobalt catalyst, which has been used beforehand, for example over several weeks or months, for amination of bioethanol and has been poisoned with sulfur in the process, the subsequent amination of isopropanol to MIPA is possible with conversions and selectivities just as high as when the same catalyst was used in fresh form. With acetone as the direct feed for the MIPA preparation, in contrast, this was not achievable due to formation of numerous by-products. The result is also surprising because the isopropanol amination is mechanistically closely related to the acetone amination because the isopropanol amination proceeds via acetone as an intermediate (cf., for example, E. J. Schwoegel et al., J. Am. Chem. Soc., 1939, pages 3499-3502).

Advantageously, it is possible in accordance with the invention to prepare ethylamine (EA) from bioethanol and MIPA from isopropanol in campaigns in a plant in the same reactor and over the same catalyst, preference being given to preparing isopropanol by hydrogenation of acetone in a separate reactor in an upstream plant part. The hydrogenation of acetone is preferably performed during the MIPA campaigns, and isopropanol, preferably crude isopropanol, is introduced directly into the amination without further workup. This concept enables preparation of the two products, EA and MIPA, in only one plant (saving of capital costs), and at the same time use of the least expensive raw materials available in each case, bioethanol and acetone (the latter first being converted to isopropanol). Between the two reactions to give EA and MIPA, no catalyst exchange is needed, nor is any chemical catalyst treatment, more particularly any catalyst activation by sulfur removal (poison removal).

Campaign preparation of ethylamines (EA) and MIPA is understood to mean that one product or the other is in each case prepared in the same production plant and over the same catalyst within the lifetime of the catalyst within time-limited intervals ("campaigns"). In this case, during the lifetime of the catalyst, ethylamines are prepared at least once, preferably at least twice, and MIPA at least once, preferably at least twice. For example, after installation of a fresh catalyst batch, ethylamines can be produced for three months ("campaign 1") and then MIPA for four months ("campaign 2"), then ethylamines again for two months ("campaign 3"), and so forth until the end of the lifetime of the catalyst has been reached. It is also possible to prepare the same product in two successive campaigns, for example when there is a plant shutdown due to inspection or the like between the two campaigns.

Accordingly, a process has been found for preparation, especially campaign preparation, of ethylamines and monoisopropylamine (MIPA), which comprises reacting bioethanol with ammonia in the presence of hydrogen and of a heterogeneous catalyst to give ethylamines, said bioethanol having a content of sulfur and/or sulfur compounds of ≥0.1 ppm by weight (calculated S), and then reacting isopropanol with ammonia in the presence of the same catalyst and in the presence of hydrogen to give MIPA.

The reactions proceed according to the following scheme:

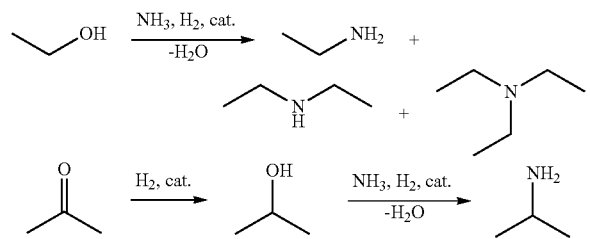

A by-product obtained in the amination of isopropanol is small amounts of di(isopropyl)amine (DTPA).

In the aminations with ammonia, the two alcohols are each converted over the very same heterogeneous catalyst (i.e. not just one of the same type). Thus, when the reactor feed is switched from bioethanol to isopropanol, there is no exchange of the catalyst, either for a catalyst of the same type or for a catalyst of another type. Preferably elevated pressure, preferably elevated temperature and the presence of hydrogen are the typical reaction conditions.

The bioethanol used in accordance with the invention is generally produced from agrochemical products such as molasses, sugarcane juice, corn starch, or from products of wood saccharification and from sulfite waste liquors by fermentation.

Preference is given to using bioethanol which has been obtained by fermentation of glucose with $CO_2$ elimination (K. Weissermel and H.-J. Arpe, Industrial Organic Chemistry, Wiley-VCH, Weinheim, 2003, p. 194; Electronic Version of Sixth Edition of Ullmann's Encyclopedia of Industrial Chemistry, 2000, Chapter Ethanol, Paragraph Fermentation).

The bioethanol is generally obtained from the fermentation broths by distillation processes: Electronic Version of Sixth Edition of Ullmann's Encyclopedia of Industrial Chemistry, 2000, Chapter Ethanol, Paragraph "Recovery and Purification".

More particularly and advantageously, in the process according to the invention, an ethanol produced by biological or biochemical means (biologically or biochemically produced ethanol=bioethanol) is used in which sulfur and/or sulfur compounds have not been depleted beforehand, for example by contacting with an adsorbent, for example silica gel, an activated alumina, a zeolite with hydrophilic properties, an activated carbon or a carbon molecular sieve.

In the process according to the invention, preference is given to using a bioethanol having a content of sulfur and/or sulfur compounds of ≥0.1 ppm by weight, or ≥0.2 ppm by weight, or ≥0.5 ppm by weight, or ≥1 ppm by weight, or ≥2 ppm by weight, or ≥5 ppm by weight, or ≥10 ppm by weight (in each case calculated S), for example determined according to Wickbold (DIN EN 41) (at S contents ≤2 ppm by weight), or determined by coulometric means to DIN 51400 part 7 (at S contents >2 ppm by weight).

The content of sulfur and/or sulfur compounds may be, for example, up to 200 ppm by weight, up to 100 ppm by weight, up to 50 ppm by weight, preferably up to 10 ppm by weight (in each case calculated S), for example determined by coulometric means to DIN 51400 part 7.

Particular preference is given to using a bioethanol having a content of sulfur and/or sulfur compounds in the range from ≥0.2 to 2 ppm by weight, for example ≥0.5 to 2 ppm by weight (in each case calculated S), for example determined according to Wickbold (DIN EN 41).

The sulfur compounds may be inorganic compounds such as sulfates, sulfites, and/or organic compounds, especially the symmetric and/or unsymmetric $C_{2-10}$-dialkyl sulfides, particularly $C_{2-6}$-dialkyl sulfides, such as diethyl sulfide, di-n-propyl sulfide, diisopropyl sulfide, very particularly dimethyl sulfide, $C_{2-10}$-dialkyl sulfoxides such as dimethyl sulfoxide, diethyl sulfoxide, dipropyl sulfoxide, 3-methylthio-1-propanol and/or S-containing amino acids such as methionine and S-methylmethionine.

In particular embodiments, a bioethanol is used which has, in addition to the above-mentioned content of sulfur and/or sulfur compounds,
a content of $C_{3-4}$-alkanols in the range of 1-5000 ppm by weight, particularly 5-3000 ppm by weight, very particularly 10-2000 ppm by weight,
a content of methanol in the range of 1-5000 ppm by weight, particularly 5-3000 ppm by weight, very particularly 20-1000 ppm by weight, and
a content of ethyl acetate in the range of 1-5000 ppm by weight, particularly 5-3000 ppm by weight, very particularly 10-2000 ppm by weight.

The content of $C_{3-4}$-alkanols (such as n-propanol, isopropanol, n-butanol, isobutanol, tertbutanol), methanol and ethyl acetate is determined, for example, by means of gas chromatography (30 m DB-WAX column, internal diameter: 0.32 mm, film thickness: 0.25 μm, FID detector, temperature program: 35° C. (5 min), heating rate 10° C./min, 200° C. (8 min)).

The sulfur content of the catalyst at the end of the period over which the reaction of bioethanol with ammonia is preferably performed is <700 ppm by weight, particularly <600 ppm by weight, more particularly <500 ppm by weight, for example 100 to <700 ppm by weight, particularly 150 to <600 ppm by weight.

For example, this period in the case of use of 0.1 kg of bioethanol/(kg$_{cat.}$·h) with a content of sulfur and/or sulfur compounds of 0.5 ppm by weight (calculated S) in the case of full adsorption of the S on the catalyst is 4000 hours, in order to bring about a sulfur content of the catalyst of 200 ppm by weight.

The catalyst used in the process according to the invention preferably comprises one or more metals of group VIII and/or IB of the Periodic Table of the Elements (Chemical Abstracts Service group notation).

Examples of such metals are Cu, Co, Ni and/or Fe, and also noble metals such as Ru, Pt, Pd, and Re. The catalysts may be doped, for instance with Ag, Zn, In, Mn, alkali metals (Li, Na, K, Rb, Cs) and/or Mo.

The heterogeneous catalyst used in the process according to the invention comprises preferably Cu and/or Ni and/or Co, preferably Cu and Ni, and also preferably Cu and Ni and Co.

Preference is given, for example, to heterogeneous catalysts whose nickel content is more than 90% by weight, particularly more than 95% by weight, based in each case on any and all metals of group VIII of the Periodic Table (Chemical Abstracts Service group notation) present.

Preference is also given, for example, to heterogeneous catalysts whose cobalt content is more than 90% by weight, particularly more than 95% by weight, based in each case on any and all metals of group VIII of the Periodic Table (Chemical Abstracts Service group notation) present.

For example, Raney nickel and Raney cobalt are suitable catalysts, and these catalysts may also be doped with further metals, such as Cr and/or Mo and/or Fe and/or other metals of group VIII of the Periodic Table (Chemical Abstracts Service group notation).

For supported heterogeneous catalysts, the support materials used for the active metals are preferably aluminum oxide (gamma, delta, theta, alpha, kappa, chi or mixtures thereof), silicon dioxide, zirconium dioxide, titanium dioxide, zeolites, aluminosilicates, etc., and mixtures of these supports.

The catalysts can be prepared by known processes, for example precipitation, precipitative application, impregnation.

The heterogeneous catalyst preferably comprises an oxidic support material for the active metals, preferably silicon dioxide, aluminum oxide (gamma, delta, theta, alpha, kappa, chi or mixtures thereof), titanium dioxide and/or zirconium dioxide (preferably monoclinic, tetragonal or cubic polymorph). A particularly preferred support material is aluminum oxide, especially gamma-aluminum oxide.

In the process according to the invention, the catalysts are preferably used in the form of catalysts which consist only of catalytically active composition and optionally a shaping assistant (for example graphite or stearic acid), if the catalyst is used as a shaped body, i.e. do not comprise any further catalytically active accompanying substances.

In this context, the oxidic support material, for example aluminum oxide ($Al_2O_3$), zirconium dioxide ($ZrO_2$), is considered to form part of the catalytically active composition.

The catalysts are used in such a way that the catalytically active composition ground to powder is introduced into the reaction vessel, or in such a way that the catalytically active composition, after grinding, mixing with shaping assistants, shaping and heat treatment, is arranged in the reactor in the form of shaped catalyst bodies—for example in the form of tablets, spheres, rings, extrudates (e.g. strands).

The concentration figures (in % by weight) of the components of the catalyst are each based—unless stated otherwise—on the catalytically active composition of the finished catalyst after the last heat treatment thereof and before the reduction thereof with hydrogen.

The catalytically active composition of the catalyst, after the last heat treatment thereof and before the reduction thereof with hydrogen, is defined as the sum of the compositions of the catalytically active constituents and of the abovementioned catalyst support materials and comprises essentially the following constituents:

silicon dioxide ($SiO_2$), aluminum oxide ($Al_2O_3$), titanium dioxide ($TiO_2$) and/or zirconium dioxide ($ZrO_2$), and oxygen compounds of copper and/or of nickel and/or of cobalt.

The sum of the abovementioned constituents of the catalytically active composition is typically 70 to 100% by weight, preferably 80 to 100% by weight, more preferably 90 to 100% by weight, particularly >95% by weight, very particularly >98% by weight, especially >99% by weight, for example more preferably 100% by weight.

The catalytically active composition of the inventive catalysts and of those used in the process according to the invention may further comprise one or more elements (oxidation state 0) or the inorganic or organic compounds thereof, selected from groups I A to VI A and I B to VII B and VIII of the Periodic Table (Chemical Abstracts Service group notation).

Examples of such elements or compounds thereof are: transition metals such as Mn or $MnO_2$, Mo or $MoO_3$, W or tungsten oxides, Ta or tantalum oxides, Nb or niobium oxides or niobium oxalate, V or vanadium oxides or vanadyl pyrophosphate; lanthanides such as Ce or $CeO_2$ or Pr or $Pr_2O_3$; alkaline earth metal oxides such as SrO; alkaline earth metal carbonates such as $MgCO_3$, $CaCO_3$ and $BaCO_3$; alkali metal oxides such as $Na_2O$, $K_2O$; alkali metal carbonates such as $Li_2CO_3$, $Na_2CO_3$ and $K_2CO_3$; boron oxide ($B_2O_3$).

Preferably, the catalytically active composition of the catalyst used in the process according to the invention does not comprise any rhenium, any ruthenium, any iron and/or any zinc, in each case either in metallic form (oxidation state=0) or in an ionic form (oxidation state≠0), especially oxidized form.

Preferably, the catalytically active composition of the catalyst used in the process according to the invention does not comprise any silver, either in metallic form (oxidation state=0) or in an ionic form (oxidation state≠0), especially oxidized form.

Preferred heterogeneous catalysts comprise, in their catalytically active composition before treatment with hydrogen, 20 to 90% by weight, preferably 40 to 85% by weight, more preferably 60 to 80% by weight, of oxygen compounds of aluminum, calculated as $Al_2O_3$, 1 to 30% by weight, preferably 2 to 25% by weight, more preferably 3 to 20% by weight, of oxygen compounds of copper, calculated as CuO, 1 to 40% by weight, preferably 3 to 30% by weight, more preferably 5 to 20% by weight, of oxygen compounds of nickel, calculated as NiO, particular preference being given to a molar ratio of nickel to copper of greater than 1, preferably of greater than 1.2, more preferably of 1.8 to 8.5, and 1 to 40% by weight, preferably 3 to 30% by weight, more preferably 5 to 20% by weight, of oxygen compounds of cobalt, calculated as CoO.

The oxygen compounds of nickel, of cobalt and of copper, each calculated as NiO, CoO and CuO, are preferably present in total amounts of 10 to 80% by weight, more preferably 15 to 60% by weight, most preferably 20 to 40% by weight, in the catalytically active composition (before the treatment with hydrogen), particular preference being given to a molar ratio of nickel to copper of greater than 1.

Particularly preferred heterogeneous catalysts comprise, in their catalytically active composition before treatment with hydrogen, 20 to 85% by weight, preferably 20 to 65% by weight, more preferably 22 to 40% by weight, of oxygen compounds of zirconium, calculated as $ZrO_2$, 1 to 30% by weight, more preferably 2 to 25% by weight, of oxygen compounds of copper, calculated as CuO, 14 to 70% by weight, preferably 15 to 50% by weight, more preferably 21 to 45% by weight, of oxygen compounds of nickel, calculated as NiO, preference being given to a molar ratio of nickel to copper of greater than 1, especially of greater than 1.2, very particularly of 1.8 to 8.5, and 0 to 5% by weight, particularly 0.1 to 3% by weight, of oxygen compounds of molybdenum, calculated as $MoO_3$.

In a further variant, these preferred catalysts additionally comprise, in their catalytically active composition before treatment with hydrogen, 15 to 50% by weight, more preferably 21 to 45% by weight, of oxygen compounds of cobalt, calculated as CoO.

The oxygen compounds of copper, of nickel and optionally of cobalt, in each case calculated as CuO, NiO and CoO, of the preferred catalysts are generally present in total amounts of 15 to 80% by weight, preferably 35 to 80% by weight, more preferably 60 to 78% by weight, in the catalytically active composition (before the treatment with hydrogen), particular preference being given to a molar ratio of nickel to copper of greater than 1.

Further preferred heterogeneous catalysts in the process according to the invention are
catalysts which are disclosed in DE 19 53 263 A (BASF AG) and comprise cobalt, nickel and copper and aluminum oxide and/or silicon dioxide with a metal content of 5 to 80% by weight, especially 10 to 30% by weight, based on the overall catalyst, said catalysts comprising, calculated on the metal content, 70 to 95% by weight of a mixture of cobalt and nickel and 5 to 30% by weight of copper, and where the weight ratio of cobalt to nickel is 4:1 to 1:4, especially 2:1 to 1:2, for example the catalyst which is used in the examples therein and has the composition of 10% by weight of CoO, 10% by weight of NiO and 4% by weight of CuO on $Al_2O_3$,
catalysts which are disclosed in EP 382 049 A (BASF AG) or are preparable correspondingly and whose catalytically active composition before treatment with hydrogen comprises 20 to 85% by weight, preferably 70 to 80% by weight, of $ZrO_2$ and/or $Al_2O_3$, 1 to 30% by weight, preferably 1 to 10% by weight, of CuO, and 1 to 40% by weight, preferably 5 to 20% by weight, of each of CoO and NiO, for example the catalysts which are described in loc. cit. on page 6 and have the composition of 76% by weight of Zr, calculated as $ZrO_2$, 4% by weight of Cu, calculated as CuO, 10% by weight of Co, calculated as CoO, and 10% by weight of Ni, calculated as NiO, catalysts which are disclosed in EP 963 975 A (BASF AG) and whose catalytically active composition before treatment with hydrogen comprises 22 to 40% by weight of $ZrO_2$, 1 to 30% by weight of oxygen compounds of copper, calculated as CuO, 15 to 50% by weight of oxygen compounds of nickel, calculated as NiO, where the molar Ni:Cu ratio is greater than 1, 15 to 50% by weight of oxygen compounds of cobalt, calculated as CoO, 0 to 10% by weight of oxygen compounds of aluminum and/or of manganese, calculated as $Al_2O_3$ and $MnO_2$ respectively, and no oxygen compounds of molybdenum, for example the catalyst A which is disclosed in loc. cit., page 17, and has the composition of 33% by weight of Zr, calculated as $ZrO_2$, 28% by weight of Ni, calculated as NiO, 11% by weight of Cu, calculated as CuO, and 28% by weight of Co, calculated as CoO, catalysts which are disclosed in EP 696 572 A (BASF AG) and whose catalytically active composition before reduction with hydrogen comprises 20 to 85% by weight of $ZrO_2$, 1 to 30% by weight of oxygen compounds of copper, calculated as CuO, 30 to 70% by weight of oxygen compounds of nickel, calculated as NiO, 0.1 to 5% by weight of oxygen compounds of molybdenum, calculated as $MoO_3$, and 0 to 10% by weight of oxygen compounds of aluminum and/or of manganese, calculated as $Al_2O_3$ and $MnO_2$ respectively, for example the catalyst which is disclosed in loc. cit., page 8, and has the composition of 31.5% by weight of $ZrO_2$, 50% by weight of NiO, 17% by weight of CuO and 1.5% by weight of $MoO_3$, catalysts which are described in EP 1 270 543 A1 (BASF AG) and comprise at least one element or a compound of an element from groups VIII and IB of the Periodic Table (Chemical Abstracts Service group notation), catalysts which are described in EP 1 431 273 A (BASF AG) and which have been produced by precipitation of catalytically active components onto monoclinic, tetragonal or cubic zirconium dioxide, catalysts described in EP 636 409 A1 (BASF AG); see especially illustrative catalysts A to E therein, whose catalytically active composition consists of 55 to 98% by weight of cobalt, 0.2 to 15% by weight of phosphorus, 0.2 to 15% by weight of manganese and 0.2 to 15% by weight of alkali metal (particularly sodium), in each case calculated as the oxide, the catalyst composition being calcined in a first step at final temperatures of 550 to 750° C., and in a second step at final temperatures of 800 to 1000° C., and cobalt catalysts as described in U.S. Pat. No. 4,314,084 A (Air Products and Chem., Inc.), i.e. comprising a group VIII metal (Chemical Abstracts Service group notation), particularly cobalt, supported on essentially neutral aluminum oxide, said support including an alkaline earth metal, particularly Ca, Ba or Mg, especially the cobalt catalyst which is specified in example 1 and comprises approx. 34% by weight of cobalt and an essentially pH-neutral $Al_2O_3$ support.

The catalysts produced/purchased can be stored as such. Before they are used as catalysts in the process according to the invention, they are pre-reduced by treatment with hydrogen (=activation of the catalyst). They can, however, also be used without pre-reduction, in which case they are reduced (=activated) by the hydrogen present in the reactor under the conditions of the process according to the invention.

For activation, the catalyst is preferably exposed to a hydrogenous atmosphere or to a hydrogen atmosphere at a temperature in the range from 100 to 500° C., particularly 150 to 400° C., very particularly 180 to 300° C., over a period of at least 25 min, particularly at least 60 min. The period of activation of the catalyst may be up to 1 h, particularly up to 12 h, especially up to 24 h.

This activation reduces at least a portion of the oxygen-metal compounds present in the catalysts to the corresponding metals, such that they are present in the active form of the catalyst together with the various different oxygen compounds.

Preparation of Ethylamines from Bioethanol and Ammonia:

The reaction is preferably performed at an absolute pressure in the range from 10 to 100 bar, particularly 15 to 80 bar, more particularly 20 to 70 bar.

The reaction is preferably effected at a temperature in the range from 130 to 230° C., particularly 150 to 225° C., more particularly 180 to 220° C.

The catalyst space velocity is preferably in the range from 0.05 to 0.50 kg/l·h, particularly 0.10 to 0.35 kg/l·h, more particularly 0.15 to 0.25 kg/l·h [kg of bioethanol/(liter of catalyst·hour)].

(liter of catalyst=catalyst bed volume)

The amount of hydrogen used is preferably in the range from 50 to 350 l (STP)/l·h, particularly 100 to 250 l (STP)/l·h, more particularly 120 to 200 l (STP)/l·h, very particularly 150 to 180 l (STP)/l·h [standard liter/(liter of catalyst·hour)]

(l(STP)=standard liters=volume converted to standard conditions (20° C., 1 bar absolute)).

The reaction is preferably performed at a molar $NH_3$:ethanol ratio in the range from 0.4 to 10 mol/mol, particularly 0.5 to 5 mol/mol, more particularly 0.6 to 2 mol/mol.

The process can be performed batchwise or preferably continuously as follows, the catalyst preferably being arranged as a fixed bed in the reactor.

The reaction is preferably performed in a tubular reactor or shell and tube reactor.

The amination can be performed in the liquid phase or in the gas phase. The fixed bed process is preferably in the gas phase.

In the case of working in the gas phase, the gaseous reactants (alcohol plus ammonia) are converted in a gas stream of size selected so as to be sufficient for vaporization, preferably hydrogen, at the abovementioned pressures and temperatures. Flow toward the fixed catalyst bed either from above or from below is possible. The required gas flow is preferably maintained by a cycle gas method.

Both when working in the liquid phase and when working in the gas phase, it is possible to employ relatively high temperatures and relatively high total pressures. When working in the liquid phase too, flow toward the fixed catalyst bed is possible either from above or from below. The pressure in the reaction vessel, which is the sum total of the partial pressures of the aminating agent, of the alcohol and of the reaction products formed, and of any solvent used in addition at the temperatures specified, is appropriately increased to the desired reaction pressure by injecting hydrogen.

Both in the case of continuous operation in the liquid phase and in the case of continuous operation in the gas phase, the excess aminating agent can be circulated together with the hydrogen.

When the catalyst is arranged as a fixed bed, it may be advantageous for the selectivity of the reaction to mix the shaped catalyst bodies with inert random packings in the reactor, effectively "diluting" them. The proportion of the random packings in such catalyst preparations may be 20 to 80, particularly 30 to 60 and especially 40 to 50 parts by volume.

The water of reaction formed in the course of the reaction (in each case one mole per mole of alcohol group converted) generally does not have a disruptive effect on the degree of conversion, the reaction rate, the selectivity and the catalyst service life, and is therefore appropriately not removed therefrom until the reaction product is worked up, for example by distillation.

The excess aminating agent and the hydrogen are removed from the reaction output, after it has been appropriately decompressed, and the resulting amination products (ethylamines) are purified by distillation or rectification. The excess aminating agent and the hydrogen are advantageously recycled back into the reaction zone. The same applies for any incompletely converted bioethanol.

Preparation of MIPA from Isopropanol and Ammonia:

The reaction is preferably performed at an absolute pressure in the range from 10 to 100 bar, particularly 20 to 80 bar, more particularly 30 to 60 bar.

The reaction is preferably effected at a temperature in the range from 130 to 230° C., particularly 150 to 225° C., more particularly 180 to 220° C.

The catalyst space velocity is preferably in the range from 0.05 to 0.50 kg/l·h, particularly 0.07 to 0.30 kg/l·h, more particularly 0.10 to 0.25 kg/l·h [kg of isopropanol/(liter of catalyst·hour)].

(liter of catalyst=catalyst bed volume)

The amount of hydrogen used is preferably in the range from 50 to 350 l (STP)/l·h, particularly 100 to 250 l (STP)/l·h, more particularly 120 to 200 l (STP)/l·h, very particularly 150 to 180 l (STP)/l·h [standard liter/(liter of catalyst·hour)]

(l(STP)=standard liters=volume converted to standard conditions (20° C., 1 bar absolute)).

The reaction is preferably performed at a molar $NH_3$:isopropanol ratio in the range from 1.0 to 10 mol/mol, particularly 1.5 to 5 mol/mol, more particularly 2 to 4 mol/mol.

The process can be performed batchwise or preferably continuously as follows, the catalyst preferably being arranged as a fixed bed in the reactor.

The reaction is preferably performed in a tubular reactor or shell and tube reactor.

The amination can be performed in the liquid phase or in the gas phase. The fixed bed process is preferably in the gas phase.

In the case of working in the gas phase, the gaseous reactants (alcohol plus ammonia) are converted in a gas stream of size selected so as to be sufficient for vaporization, preferably hydrogen, at the abovementioned pressures and temperatures. Flow toward the fixed catalyst bed either from above or from below is possible. The required gas flow is preferably maintained by a cycle gas method.

Both when working in the liquid phase and when working in the gas phase, it is possible to employ relatively high temperatures and relatively high total pressures. When working in the liquid phase too, flow toward the fixed catalyst bed is possible either from above or from below. The pressure in the reaction vessel, which is the sum total of the partial pressures of the aminating agent, of the alcohol and of the reaction products formed, and of any solvent used in addition at the temperatures specified, is appropriately increased to the desired reaction pressure by injecting hydrogen.

Both in the case of continuous operation in the liquid phase and in the case of continuous operation in the gas phase, the excess aminating agent can be circulated together with the hydrogen.

When the catalyst is arranged as a fixed bed, it may be advantageous for the selectivity of the reaction to mix the shaped catalyst bodies with inert random packings in the reactor, effectively "diluting" them. The proportion of the random packings in such catalyst preparations may be 20 to 80, particularly 30 to 60 and especially 40 to 50 parts by volume.

The water of reaction formed in the course of the reaction (in each case one mole per mole of alcohol group converted) generally does not have a disruptive effect on the degree of conversion, the reaction rate, the selectivity and the catalyst service life, and is therefore appropriately not removed therefrom until the reaction product is worked up, for example by distillation.

The excess aminating agent and the hydrogen are removed from the reaction output, after it has been appropriately decompressed, and the resulting amination product (MIPA) is purified by distillation or rectification. The excess aminating agent and the hydrogen are advantageously recycled back into the reaction zone. The same applies for any incompletely converted isopropanol.

Preparation of Isopropanol from Acetone (Hydrogenation):

The preferred catalyst is an aluminum oxide-supported Cu catalyst.

Preference is also given to copper- and chromium-containing catalysts (Cu—Cr catalysts). Also preferred is the shaped copper chromite(III) catalyst described in EP 563 327 A=WO 92/10290 A1 (Engelhard Corp.), prepared from a mixture comprising 20 to 80% by weight of copper chromite(III) in which some or all of the copper chromite (III) preferably has the formula $CuO \cdot CuCr2O_4$, and 20 to 80% by weight of at least one extrudable inorganic binder material, in which the catalyst has a surface area of 20 to 225 $m^2/g$ and the total pore volume of the pores having a diameter up to 9500 nanometers (95 000 angström) in the catalyst is 0.35 to 1 $cm^3/g$; see especially the illustrative catalysts therein (examples 1-6). Likewise suitable is the commercially available extruded copper chromite(III) catalyst "Cu-1230E ⅛ in." specified in WO 92/10290 A1 (page 13 line 3).

Preferred catalysts are likewise the catalysts taught for acetone hydrogenation in EP 361 755 A2 (Mitsui Petrochem. Ind.), column 6.

The reaction is preferably performed at an absolute pressure in the range from 10 to 100 bar, particularly 30 to 90 bar, more particularly 40 to 80 bar.

The reaction is preferably effected at a temperature in the range from 40 to 170° C., particularly 50 to 160° C. The temperature in continuous mode is more particularly in the range from 50 to 80° C. at the reactor inlet and 120 to 150° C. at the reactor outlet.

The catalyst space velocity is preferably in the range from 0.1 to 0.7 kg/l·h, particularly 0.15 to 0.6 kg/l·h, more particularly 0.2 to 0.5 kg/l·h [kg of acetone/(liter of catalyst·hour)].

(liter of catalyst=catalyst bed volume)

The amount of hydrogen used is preferably in the range from 50 to 350 l (STP)/l·h, particularly 100 to 250 l (STP)/l·h, more particularly 120 to 200 l (STP)/l·h, very particularly 150 to 180 l (STP)/l·h [standard liter/(liter of catalyst·hour)]

(l(STP)=standard liters=volume converted to standard conditions (20° C., 1 bar absolute)).

The reaction is preferably performed at a molar $H_2$:acetone ratio in the range from 1.0 to 3.0 mol/mol, particularly 1.0 to 1.5 mol/mol, more particularly 1.0 to 1.2 mol/mol.

The process can be performed batchwise or preferably continuously as follows, the catalyst preferably being arranged as a fixed bed in the reactor.

The reaction is preferably performed in a tubular reactor or shell and tube reactor.

The hydrogenation can be performed in the liquid phase or in the gas phase.

Both when working in the liquid phase and when working in the gas phase, it is possible to employ relatively high temperatures and relatively high total pressures. The pressure in the reaction vessel, which is the sum total of the partial pressures of the acetone and of the reaction products formed, and of any solvent used in addition at the temperatures specified, is appropriately increased to the desired reaction pressure by injecting hydrogen.

Both in the case of continuous operation in the liquid phase and in the case of continuous operation in the gas phase, the excess aminating agent can be circulated together with the hydrogen.

When the catalyst is arranged as a fixed bed, it may be advantageous for the selectivity of the reaction to mix the shaped catalyst bodies with inert random packings in the reactor, effectively "diluting" them. The proportion of the random packings in such catalyst preparations may be 20 to 80, particularly 30 to 60 and especially 40 to 50 parts by volume.

The reaction output of the acetone hydrogenation is preferably used directly, i.e. without a further workup step such as purification/distillation, in the amination for MIPA preparation.

The reaction is more preferably conducted in the trickle phase in a shaft reactor. In this case, both the liquid (acetone+ return isopropanol) and the gas (hydrogen) are fed into the reactor from the top. In the course of passage through the reactor, the exothermicity of the reaction results in an adiabatic temperature rise which is limited to 30 to 100° C. due to the dilution of the acetone by the isopropanol circulated. Downstream of the reactor outlet, the reaction mixture passes through a cooler, before the gas and liquid phases are separated in a separator. A portion of the liquid phase, for example <50% by weight, is purified or preferably fed directly (under pressure) into the amination (to give MIPA). The other portion of the liquid phase is preferably recycled into the hydrogenation as return isopropanol.

All pressure figures are based on absolute pressure.
All ppm figures are based on weight.

EXAMPLES

Catalyst 'A'

Catalyst 'A', a $Cu/Ni/Mo/ZrO_2$ catalyst, as disclosed in EP 696 572 A1 (BASF AG), see example 1 therein, was prepared by precipitation, filtration, heat treatment and tabletting (6×3 mm tablets).

The catalyst had the following composition before it was treated (activated) with hydrogen: 50% by weight of NiO, 17% by weight of CuO and 1.5% by weight of $MoO_3$ on $ZrO_2$.

Example 1

Sequential Amination of Bioethanol, Acetone, Bioethanol and Isopropanol Over an Ni and Cu Catalyst a) Operation with Bioethanol A vertical fixed bed reactor was charged with 800 ml (1313 g) of the tabletted Ni/Cu catalyst 'A'. After activation with hydrogen (250° C., ambient pressure, 24 h), 120 g/h of biologically produced ethanol (bioethanol) which additionally comprised small proportions of ethylamines and water (composition in % by weight: 87% ethanol, 5.7% ethylamines, 7% water, 1 ppm of sulfur, higher alcohols totalling <0.3%)— corresponding to a catalyst space velocity of 0.15 kg/(l·h)— and 57 g/h of ammonia, and also 185 l (STP)/h of hydrogen, were passed through the catalyst bed from the top downward in straight pass (l(STP)=standard liters=volume converted to standard conditions (20° C., 1 bar)). The pressure was 66 bar; the temperature was 185-188° C. Bypass high-pressure samples were taken from the reaction mixture downstream of the reactor (100 ml pressure cylinder) and decompressed into 40 ml of water in the laboratory. The aqueous solutions were analyzed by gas chromatography: RTX-5 amine column (l=30 m; ID=0.32 mm; film thickness (df)=1.5 µm); 40° C. (10 min); to 280° C. at 10° C./min; 280° C. (5 min); carrier gas He; detector FID. The results are reported as percentages by weight of the organic component. The experiment was conducted for approx. 2900 h, and 91-94% ethylamines and 6-9% unconverted ethanol were obtained.

During this run time, the catalyst had been contaminated with a total of 356 kg of bioethanol with an approximate sulfur content of 1 ppm, i.e. with 356 mg, corresponding to 271 ppm by weight on the catalyst, of sulfur.

b) Operation with Acetone

Subsequently, 128 g/h of acetone (space velocity 0.16 kg/(l·h)), 109 g/h of ammonia and hydrogen were conducted into the reactor for approx. 180 h (pressure 40 bar).

Bypass high-pressure samples of the reaction mixture were taken downstream of the reactor (100 ml pressure cylinder) and decompressed into 40 ml of water in the laboratory. The aqueous solutions were analyzed by gas chromatography: DB1 column (l=30 m; ID=0.32 mm; film thickness (df)=3 μm); 50° C. (10 min); to 280° C. at 10° C./min; 280° C. (17 min); carrier gas He; detector FID. The results are reported in the following table as percentages by weight:

| Run time [h] | Temp. [° C.] | H2 [l(STP)/h] | MIPA [%] | isopropanol [%] | DIPA [%] | Total C6amines [%] |
|---|---|---|---|---|---|---|
| 24 | 110 | 180 | 83.79 | 3.23 | 0.99 | 6.15 |
| 36 | 120 | 180 | 86.38 | 3.52 | 1.45 | 5.83 |
| 48 | 120 | 180 | 87.11 | 3.45 | 1.47 | 5.46 |
| 60 | 130 | 180 | 85.70 | 4.03 | 2.33 | 5.07 |
| 84 | 130 | 180 | 85.76 | 4.09 | 2.43 | 4.57 |
| 108 | 130 | 300 | 82.07 | 6.01 | 4.87 | 2.82 |
| 120 | 130 | 300 | 83.42 | 5.19 | 4.81 | 2.70 |
| 132 | 130 | 300 | 82.69 | 4.52 | 4.68 | 2.50 |
| 156 | 120 | 300 | 85.73 | 4.26 | 3.81 | 3.28 |
| 168 | 110 | 300 | 87.69 | 3.94 | 2.03 | 3.74 |
| 180 | 110 | 300 | 85.47 | 4.44 | 1.77 | 4.51 |

Acetone was converted fully over the run time.

It is clear that acetone can be aminated to MIPA only in poor yields over a catalyst sulfurized by prior operation with bioethanol, and condensation products (C6 amines) in particular are formed in a considerable amount.

c) Operation with Bioethanol (Inventive)

Thereafter, the catalyst was operated again with bioethanol (analogous conditions to those above) for approx. 500 h.

After this time, a total of 414 kg of bioethanol with a sulfur content of 1 ppm had thus been run through the catalyst bed, i.e., assuming complete adsorption, 414 mg, corresponding to 315 ppm by weight, of sulfur were present on the catalyst.

d) Operation with Isopropanol

Finally, in this experiment, isopropanol (space velocities 0.13-0.16 kg/(l·h)), 109 g/h of ammonia (molar NH$_3$:isopropanol ratio=3.0 to 3.8) and 120 l (STP)/h of hydrogen were conducted into the reactor for approx. 240 h (pressure 45 bar); cf. table.

Bypass high-pressure samples of the reaction mixture were taken downstream of the reactor (100 ml pressure cylinder) and decompressed into 40 ml of water in the laboratory. The aqueous solutions were analyzed by gas chromatography as described above in b). The results are reported as percentage by weight in the following table:

| Run time [h] | Temp. [° C.] | isopropanol (feed) [g/h] | Space velocity [kg/(l·h)] | MIPA [%] | isopropanol [%] | DIPA [%] | Total C6amines [%] | C (isopropanol) [%] | S (MIPA) [%] |
|---|---|---|---|---|---|---|---|---|---|
| 24 | 180 | 128 | 0.16 | 88.16 | 6.82 | 2.39 | 0.00 | 93.18 | 94.61 |
| 36 | 180 | 128 | 0.16 | 89.65 | 6.40 | 3.14 | 0.00 | 93.60 | 95.57 |
| 48 | 180 | 128 | 0.16 | 89.94 | 6.24 | 3.36 | 0.00 | 93.76 | 95.93 |
| 60 | 180 | 128 | 0.16 | 89.68 | 6.95 | 2.91 | 0.00 | 93.05 | 96.38 |
| 72 | 185 | 128 | 0.16 | 87.72 | 5.97 | 5.81 | 0.00 | 94.03 | 93.28 |
| 84 | 185 | 128 | 0.16 | 87.84 | 5.93 | 5.80 | 0.00 | 94.07 | 93.38 |
| 108 | 180 | 128 | 0.16 | 89.20 | 7.04 | 3.36 | 0.00 | 92.96 | 95.96 |
| 132 | 180 | 128 | 0.16 | 90.23 | 6.25 | 3.20 | 0.00 | 93.75 | 96.25 |
| 156 | 180 | 128 | 0.16 | 90.02 | 6.40 | 3.23 | 0.00 | 93.60 | 96.17 |
| 168 | 180 | 128 | 0.16 | 89.56 | 6.81 | 3.28 | 0.00 | 93.19 | 96.11 |
| 180 | 180 | 100 | 0.13 | 91.88 | 4.23 | 3.51 | 0.00 | 95.77 | 95.93 |
| 192 | 180 | 100 | 0.13 | 91.35 | 4.77 | 3.37 | 0.00 | 95.23 | 95.93 |
| 204 | 180 | 100 | 0.13 | 91.22 | 4.77 | 3.61 | 0.00 | 95.23 | 95.79 |
| 216 | 180 | 100 | 0.13 | 90.60 | 5.54 | 3.47 | 0.00 | 94.46 | 95.91 |
| 228 | 180 | 100 | 0.13 | 91.35 | 5.08 | 3.20 | 0.00 | 94.92 | 96.24 |
| 240 | 180 | 100 | 0.13 | 91.12 | 5.07 | 3.45 | 0.00 | 94.93 | 95.99 |
| 252 | 180 | 100 | 0.13 | 91.40 | 4.81 | 3.43 | 0.00 | 95.19 | 96.02 |
| 264 | 180 | 100 | 0.13 | 91.64 | 4.55 | 3.41 | 0.01 | 95.46 | 96.00 |

It is clear that amination of isopropanol can achieve much better MIPA yields than amination of acetone, more particularly with no formation of condensation products (C6 amines). The conversion in % is defined here as "100%-isopropanol [% by weight]". The selectivity in % is defined here as "quotient of MIPA [% by weight] and conversion [%], multiplied by 100".

Example 2

Comparative Example

Amination of Isopropanol to Give MIPA Over a Fresh Catalyst which has not been Used Beforehand for the Amination of Bioethanol A vertical fixed bed reactor was charged with 130 ml of the tabletted Ni/Cu catalyst 'A'. After activation with hydrogen, 19 g/h of isopropanol—corresponding to a catalyst space velocity of 0.15 kg/(l·h)—and 18 g/h of ammonia (molar NH$_3$:isopropanol ratio=3.3), and 29 l (STP)/h of hydrogen were passed through the catalyst bed in straight pass. The pressure was 45 bar, the temperature 180° C. Over a run time of approx. 90 h, the following average values were obtained: 89% MIPA; 6.1% isopropanol; 5.1% di(isopropyl)amine and 0.00% condensation products (C6 amines); (GC method as described in b)). According to the definition in example 1d), the isopropanol conversion was 93.9% and the MIPA selectivity 94.8%.

It is thus clear that the amination of isopropanol to MIPA over a catalyst previously used for the amination of sulfur-containing bioethanol leads to results which are at least as good in terms of conversion and selectivity as the amination of isopropanol to MIPA over a fresh catalyst.

Example 3

Sequential Amination of Bioethanol and Isopropanol Over a Cobalt Catalyst a) Operation with Bioethanol A vertical fixed bed reactor was charged with 800 ml (773 g) of the G-62RS catalyst commercially available from Süd-Chemie (see "General Catalogue Süd-Chemie Catalysts" (2007)). After activation with hydrogen at up to 240° C. and 40 bar (for approx. 24 h), 120-200 g/h of biologically produced ethanol which additionally comprised small proportions of ethylamines and water (composition: 89% ethanol, 3.7% ethylamines, 7% water, 1 ppm of sulfur, higher alcohols totalling <0.3%)—corresponding to a catalyst space velocity of 0.15-0.25 kg/(l·h)—and 57-96 g/h of ammonia, and also between 130 and 275 l (STP)/h of hydrogen, were passed through the catalyst bed in straight pass from the top downward. The pressure was 66 bar, the temperature 175-194° C. Bypass high-pressure samples of the reaction mixture were taken downstream of the reactor (100 ml pressure cylinder) and decompressed into 40 ml of water in the laboratory. The aqueous solutions were analyzed by gas chromatography: RTX-5 amine column (l=30 m; ID=0.32 mm; film thickness (df)=1.5 μm); 40° C. (10 min); to 280° C. at 10° C./min; 280° C. (5 min); carrier gas He; detector FID. The results are reported as percentages by weight of the organic component. The experiment was conducted for approx. 2500 h, and 85-96% ethylamines and 3-14% unconverted ethanol were obtained.

During this run time, the catalyst had been contaminated with a total of 347 kg of bioethanol with an approximate sulfur content of 1 ppm, i.e. with 347 mg of sulfur (corresponding to 449 ppm by weight).

b) Operation with Isopropanol

Subsequently, in this experiment, isopropanol (space velocities 0.13-0.17 kg/(l·h)), 93-118 g/h of ammonia (molar $NH_3$:iso-propanol ratio=2.8 to 3.9) and 120-126 l (STP)/h of hydrogen were conducted into the reactor for approx. 580 h (pressure 45 bar); cf. table.

Bypass high-pressure samples of the reaction mixture were taken downstream of the reactor (100 ml pressure cylinder) and decompressed into 40 ml of water in the laboratory. The aqueous solutions were analyzed by gas chromatography as described above in example 1b. The results are reported as percentages by weight in the following table:

| Run time [h] | Temp. [° C.] | isopropanol (feed) [g/h] | NH3 [g/h] | MIPA [%] | isopropanol [%] | DIPA [%] | Total C6amines [%] | C (isopropanol) [%] | S (MIRA) [%] |
|---|---|---|---|---|---|---|---|---|---|
| 48 | 180 | 128 | 109 | 85.11 | 11.99 | 2.19 | 0.00 | 88.02 | 96.70 |
| 72 | 180 | 128 | 109 | 84.44 | 11.88 | 2.21 | 0.00 | 88.13 | 95.82 |
| 96 | 185 | 128 | 109 | 86.04 | 9.38 | 3.57 | 0.00 | 90.62 | 94.95 |
| 120 | 185 | 128 | 109 | 86.18 | 9.85 | 3.57 | 0.00 | 90.15 | 95.59 |
| 144 | 188 | 123 | 118 | 86.51 | 9.59 | 3.58 | 0.00 | 90.41 | 95.69 |
| 168 | 188 | 126 | 109 | 86.41 | 8.77 | 4.47 | 0.00 | 91.23 | 94.72 |
| 216 | 193 | 130 | 93 | 84.69 | 7.83 | 7.10 | 0.00 | 92.17 | 91.89 |
| 240 | 193 | 132 | 109 | 84.80 | 7.94 | 6.88 | 0.00 | 92.06 | 92.12 |
| 264 | 193 | 132 | 105 | 84.37 | 7.78 | 7.41 | 0.00 | 92.22 | 91.49 |
| 288 | 193 | 133 | 105 | 85.37 | 8.18 | 6.09 | 0.00 | 91.82 | 92.97 |
| 312 | 193 | 130 | 111 | 83.96 | 8.54 | 7.07 | 0.00 | 91.46 | 91.80 |
| 336 | 193 | 100 | 107 | 87.23 | 5.78 | 6.57 | 0.00 | 94.22 | 92.58 |
| 360 | 193 | 100 | 108 | 86.87 | 5.78 | 6.31 | 0.00 | 94.22 | 92.19 |
| 432 | 193 | 100 | 109 | 85.14 | 5.21 | 8.04 | 0.00 | 94.79 | 89.82 |
| 456 | 193 | 100 | 109 | 85.66 | 5.18 | 7.76 | 0.00 | 94.82 | 90.34 |
| 480 | 185 | 100 | 109 | 88.81 | 6.61 | 3.77 | 0.00 | 93.39 | 95.10 |
| 552 | 185 | 100 | 109 | 88.97 | 6.38 | 4.01 | 0.00 | 93.62 | 95.03 |
| 576 | 185 | 100 | 109 | 88.50 | 6.61 | 3.97 | 0.01 | 93.39 | 94.76 |

It is clear that the amination of isopropanol to MIPA proceeds in high selectivities and more particularly with avoidance of condensation products (C6 amines), even though it has been performed over a catalyst which had been used beforehand for the amination of sulfur-containing bioethanol and was thus sulfur-contaminated. The conversion in % is defined here as "100%-isopropanol [% by weight]". The selectivity in % is defined here as "quotient of MIPA [% by weight] and conversion [%], multiplied by 100".

Methods of Sulfur Determination in Bioethanol

The method of coulometry is described in DIN 51400-7.

The sample preparation for the combustion according to Wickbold is described, for example, in DIN 51408-1, and can also be read about in "Quantitative organische Elementaranalyse" [Quatitative organic elemental analysis"], Friedrich Ehrenberger, ISBN 3-527-28056-1, page 424 ff. The sulfate formed in the combustion and absorbed is analyzed by means of ion chromatography. Accompanying literature is, for example, "lonenchromatographie" [Ion chromatography], Joachim Weiβ, ISBN 3-327-28702-7, page 68 ff.

The invention claimed is:

1. A process for preparing ethylamines and monoisopropylamine (MIPA), which comprises reacting bioethanol with ammonia in the presence of hydrogen and of a heterogeneous catalyst to give ethylamines, said bioethanol having a content of sulfur and/or sulfur compounds of ≥0.1 ppm by weight (calculated S), and then reacting isopropanol with ammonia in the presence of the same catalyst and in the presence of hydrogen to give MIPA.

2. The process according to claim 1, wherein the sulfur content of the catalyst at the end of the period over which the reaction of bioethanol with ammonia is performed is <700 ppm by weight.

3. The process according to claim 1, wherein the reactions are performed in the presence of a heterogeneous copper and/or nickel and/or cobalt catalyst.

4. The process according to claim 1, wherein the reactions are performed in the presence of a heterogeneous catalyst having a nickel content of more than 90% by weight, based on any and all metals of group VIII of the Periodic Table present.

5. The process according to claim 1, wherein the reactions are performed in the presence of a heterogeneous catalyst having a cobalt content of more than 90% by weight, based on any and all metals of group VIII of the Periodic Table present.

6. The process according to claim 1, wherein the reactions are performed in the presence of a heterogeneous copper and nickel catalyst.

7. The process according to claim 1, wherein the reactions are performed in the presence of a heterogeneous copper and nickel and cobalt catalyst.

8. The process according to claim 1, wherein the heterogeneous catalyst comprises aluminum oxide, silicon dioxide, titanium dioxide and/or zirconium dioxide as support material.

9. The process according to claim 1, wherein the heterogeneous catalyst comprises, in its catalytically active composition before the treatment with hydrogen,
- 20 to 85% by weight of oxygen compounds of zirconium, calculated as ZrO2,
- 1 to 30% by weight of oxygen compounds of copper, calculated as CuO,
- 14 to 70% by weight of oxygen compounds of nickel, calculated as NiO, and
- 0 to 5% by weight of oxygen compounds of molybdenum, calculated as MoO3.

10. The process according to claim 1, wherein the reactions are each performed at an absolute pressure in the range from 10 to 100 bar.

11. The process according to claim 1, wherein the reactions are each performed at a temperature in the range from 130 to 230° C.

12. The process according to claim 1, wherein the reactions are each performed continuously.

13. The process according to claim 1, wherein there is no catalyst activation by sulfur removal (poison removal) between the two reactions.

14. The process according to claim 1, wherein the reactions are each performed at a catalyst space velocity in the range from 0.05 to 0.35 kg of alcohol/(liter of catalyst·hour).

15. The process according to claim 1, wherein the amount of hydrogen used is in each case in the range from 50 to 350 standard liters/(liter of catalyst·hour).

16. The process according to claim 1, wherein the molar NH3: ethanol ratio is in the range from 0.4 to 10.

17. The process according to claim 1, wherein the molar NH3: isopropanol ratio is in the range from 1.0 to 10.

18. The process according to claim 1, wherein isopropanol which has been prepared beforehand by hydrogenation of acetone in the presence of a copper and/or nickel and/or cobalt catalyst is used.

19. The process according to claim 18, wherein the reaction output of the acetone hydrogenation is used directly in the amination for MIPA preparation.

20. The process according to claim 1, wherein the reactions are each performed in the gas phase.

21. The process according to claim 1, wherein the reactions are each performed in a tubular reactor or a shell and tube reactor.

22. The process according to claim 1, wherein the catalyst is arranged as a fixed bed.

23. The process according to claim 1, wherein the bioethanol has a content of sulfur and/or sulfur compounds of ≥0.2 ppm by weight to 10 ppm by weight (calculated S).

24. The process according to claim 1, wherein the sulfur content of the catalyst at the end of the period over which the reaction of bioethanol with ammonia is performed is 150 to <600 ppm by weight.

25. The process according to claim 1, wherein there is no catalyst treatment between the two reactions.

* * * * *